(12) United States Patent
Werker et al.

(10) Patent No.: US 9,688,555 B2
(45) Date of Patent: Jun. 27, 2017

(54) BIOLOGICAL WASTEWATER TREATMENT PROCESSES THAT ENHANCES THE CAPACITY FOR POLYHYDROXYALKANOATE ACCUMULATION IN A MIXED CULTURE BIOMASS

(71) Applicant: Veolia Water Solutions & Technologies Support, Saint-Maurice (FR)

(72) Inventors: Alan Gideon Werker, Lomma (SE); Fernando Morgan-Sagastume, Malmo (SE); Simon Olof Harald Bengtsson, Dalby (SE); Maria da Graca Ejarque Albuquerque Cordeiro Pereira, Maurecourt (FR)

(73) Assignee: Veolia Water Solutions & Technologies Support, Saint Maurice (FR)

( * ) Notice: Subject to any disclaimer, the term of this patent is extended or adjusted under 35 U.S.C. 154(b) by 0 days.

(21) Appl. No.: 14/760,221

(22) PCT Filed: Jan. 10, 2014

(86) PCT No.: PCT/IB2014/058187
§ 371 (c)(1),
(2) Date: Jul. 10, 2015

(87) PCT Pub. No.: WO2014/108864
PCT Pub. Date: Jul. 17, 2014

(65) Prior Publication Data
US 2015/0353395 A1      Dec. 10, 2015

Related U.S. Application Data

(60) Provisional application No. 61/751,454, filed on Jan. 11, 2013.

(51) Int. Cl.
C02F 3/30 (2006.01)
C02F 3/12 (2006.01)
C12P 7/62 (2006.01)

(52) U.S. Cl.
CPC ............ *C02F 3/1263* (2013.01); *C02F 3/302* (2013.01); *C12P 7/62* (2013.01); *C12P 7/625* (2013.01);
(Continued)

(58) Field of Classification Search
CPC .. C02F 3/1263; C02F 2203/004; C02F 3/302; C12P 7/62; C12P 7/625; Y02W 10/15
(Continued)

(56) References Cited

U.S. PATENT DOCUMENTS

| 8,748,138 B2* | 6/2014 | Werker | C12P 7/625 |
| | | | 435/132 |
| 9,085,784 B1* | 7/2015 | Herrema | C12P 7/625 |

(Continued)

FOREIGN PATENT DOCUMENTS

| JP | H06062875 A | 3/1994 |
| WO | 2009153303 A2 | 12/2009 |

(Continued)

OTHER PUBLICATIONS

Albuquerque, M.G.E., et al., "Strategies for the development of a side stream process for polyhydroxyalkanoate (PHA) production from sugar can molasses", Journal of Biotechnology, vol. 130, pp. 411-421 (2007).

(Continued)

*Primary Examiner* — Fred Prince
(74) *Attorney, Agent, or Firm* — Coats & Bennett PLLC

(57) ABSTRACT

A method of biologically treating wastewater and, at the same time, incorporating processes that aim to increase the PHA accumulation potential of biomass used in the treat- (Continued)

ment of the wastewater. The method includes biologically treating the wastewater and enhancing PHA accumulation potential of the biomass by subjecting the biomass to a primary feast-famine process where the biomass is subjected to repeated cycles of feast and primary famine conditions. From time-to-time, the method entails deviating from the primary feast-famine process to a secondary famine process. The secondary famine process comprises subjecting the biomass to secondary famine conditions for a period of time that is substantially greater than the average time period of the primary famine conditions.

32 Claims, 10 Drawing Sheets

(52) U.S. Cl.
CPC ........ *C02F 2203/004* (2013.01); *Y02W 10/15* (2015.05)

(58) Field of Classification Search
USPC .................................. 210/605, 623, 630, 903
See application file for complete search history.

(56) References Cited

U.S. PATENT DOCUMENTS

| 2005/0045557 | A1 | 3/2005 | Daigger et al. |
| 2010/0200498 | A1 | 8/2010 | Bengtsson et al. |
| 2012/0301933 | A1 | 11/2012 | Smith et al. |
| 2013/0199997 | A1* | 8/2013 | Werker ..................... C02F 3/12 210/614 |

FOREIGN PATENT DOCUMENTS

| WO | 2011073744 A1 | 6/2011 |
| WO | 2011103286 A2 | 8/2011 |
| WO | 2012022998 A1 | 2/2012 |
| WO | 2012023114 A1 | 2/2012 |

OTHER PUBLICATIONS

Rodgers, Michael, et al., "Production of polyhydroxybutyrate by activated sludge performing enhanced biological phosphorus removal", Bioresource Technology, vol. 101, pp. 1049-1053 (2010).
Din, M. F. Md., et al., "Raw material resource for biodegradable plastic production from cafeteria wastes", Journal of Scientific & Industrial Research, vol. 71, pp. 573-578 (Aug. 2012).
Liu, Hsin-Ying, "Bioplastics Poly(hydroxyalkanoate) Production during Industrial Wastewater Treatment", XP002722437, Retrieved from the Internet: URL:http://gradworks.umi.com/33/62/3362495.html [retrieved on Mar. 28, 2014], p. 35 (2009).
Coats, Erik R., et al., "Post-anoxic denitrification driven by PHA and glycogen within enhanced biological phosphorus removal", Bioresource Technology, Jan. 1, 2011, pp. 1019-1027, vol. 102, issue 2.
Serafim, L., et al., "Optimization of Polyhydroxybutyrate Production by Mixed Cultures Submitted to Aerobic Dynamic Feeding Conditions", Biotechnology and Bioengineering, Wiley Periodicals, Inc., Jun. 16, 2004, pp. 145-160, vol. 87.
Korea Water and Wastewater Works Association, "Standard for Urban Sewage Facility", Sewerage Facility Criteria, Ministry of Environment, Jan. 1, 2011, pp. 524-525.

\* cited by examiner

BIOLOGICAL WASTEWATER TREATMENT PROCESSES THAT ENHANCES THE CAPACITY FOR POLYHYDROXYALKANOATE ACCUMULATION IN A MIXED CULTURE BIOMASS

This application is a U.S. National Stage Application of PCT Application No. PCT/IB2014/058187, with an international filing date of 10 Jan. 2014. Applicant claims priority based on U.S. Provisional Patent Application No. 61/751,454 filed 11 Jan. 2013. The subject matter of these applications is incorporated herein.

BACKGROUND

Biological treatment of wastewaters for removal of the chemical oxygen demand (COD) produces a biomass. Today, the wasted surplus biomass represents a solid waste disposal problem. An opportunity that has attracted much interest is the production of biodegradable polymers by biomass, such as that in activated sludge treating wastewater. In this way, at least part of the produced activated sludge becomes a valuable by-product that can be harvested from a biological wastewater treatment process. The harvested biomass can be made to accumulate significant levels of biopolymers and the now biopolymer-rich biomass is no longer a disposal problem but is, to the contrary, a raw material resource in the value chain towards bioplastics and/or fine chemicals. In this manner a sludge disposal problem may be turned into a renewable resource opportunity.

It is known that biomass produced in biological treatment of process waters and wastewaters can be made to accumulate biopolymers in the class of polyhydroxyalkanoates (PHAs), a group of polyesters produced by many naturally occurring species of bacteria as intermediate carbon and energy reservoirs. PHAs are biopolymers that can be recovered from biomass and converted into biodegradable plastics of commercial value that are useful for a broad range of practical applications (see for examples, US 2010/0200498, WO 2011/070544A2, WO 2011/073744A1, WO 2012/022998A1, WO 2012/023114A1).

From the body of academic and intellectual property publications (see for example Salehizadeh and Loosdrecht, Biotechnology Advances 22 (2004) 261-279), it is known that a means for enhancing the potential of biomass to accumulate PHA while treating a wastewater involves a so-called feast and famine strategy. Feast and famine means that the biological treatment is carried out such that the biomass is exposed to alternating environments of available and scarcely available substrate in the form of readily biodegradable COD (RBCOD). RBCOD may, for example, include volatile fatty acids such as acetic acid. One gram mass of acetic acid is equivalent to 1.067 grams of acetic acid as chemical oxygen demand or COD.

Under the conditions of suddenly available RBCOD during feast, RBCOD is taken up by the biomass just after being exposed to a famine environment. During feast, at least some RBCOD is converted into PHA. Under famine conditions with low RBCOD availability, the populations of bacteria in the biomass that stored at least some PHA during feast can use this internally stored PHA as a source of energy and carbon for growth and survival during famine. Thus the alternation of feast and famine environments tends to select for the survival of populations of bacteria in the biomass with ability to store PHA.

By applying feast and famine conditions, the PHA accumulation potential (PAP) of biomass can be enriched compared to typical minimal background levels found in biomass in conventional biological wastewater treatment systems. A typical minimal background PAP for activated sludge is an ability to store PHA to a level less than about 20% g-PHA/g-VSS. An enriched PAP may be considered to be an accumulation potential of about 30% or more, and preferably more than 50% g-PHA/g-VSS. A high PAP makes the accumulation process and subsequent recovery of PHA more efficient and thereby improves the overall process economy of producing PHA as a by-product of services in water quality management by biological treatment.

Production of PHA from services of water quality management can be a part of an overall biorefinery concept involving biological treatment unit processes comprising but not limited to:
 1. Optional pretreatment such as acidogenic fermentation in order to convert organic matter into RBCOD fermentation products such as volatile fatty acids (VFAs).
 2. Removal of organic contamination from the water and production of a biomass with potential for significant accumulation of PHAs or enriched PAP.
 3. Expressing the PAP of the surplus biomass from 2, by controlled accumulation of PHAs in the harvested biomass by using RBCOD coming from either the same source as used for biomass production or by using other available sources of RBCOD.
 4. Recovery and purification of the PHAs from the PHA-rich biomass produced in 3.

Typical feast and famine selection of PAP has focused on maintaining stable conditions in time of a cyclic regime of feast and famine. This is to say that the biomass is exposed to repeated cycles of feast and famine, where the total feast-famine cycle time is approximately constant, and where the famine portion is generally meant to be greater than ¾ of this cycle time. Although feast and famine selection has been repeatedly shown to enrich the PAP of a biomass produced in open mixed-cultures, results also suggest that the microbial community that comprises the biomass may adapt itself to the regime of feast-famine. By adaptation the microbial community may be less likely to directly reach its full potential of PAP during a PHA accumulation process.

SUMMARY OF THE INVENTION

The present invention relates to a method of biologically treating wastewater with biomass and, in the process of treating the wastewater, enhancing the PHA accumulation potential that is expressed by the biomass. Various biological processes can be employed. For example, the biomass may be employed to remove BOD, nitrogen, phosphorus, and a wide range of contaminants commonly found in municipal and other types of wastewater or process water streams. To enhance the PHA accumulation potential of the biomass, a primary feast-famine (selection) process is employed. The primary feast-famine process subjects the biomass to repeated cycles of feast and famine conditions. These conditions are referred to as primary feast conditions and primary famine conditions. The number of repeated cycles of feast and famine conditions can vary. In one embodiment, the biomass is exposed to at least two repeating cycles of alternating feast and famine conditions.

In addition to that the biomass is exposed to a number of alternating feast and famine cycles, the processes described herein involve the introduction of a controlled deviation or deviations from the cyclic primary feast-famine regime. The deviation process is referred to as a secondary famine process or simply a secondary perturbation. In the secondary famine process, the biomass or a portion thereof is subjected to famine conditions for a period of time substantially greater than the average primary famine period. In one embodiment, the secondary famine period is greater than the average of the proceeding primary famine periods but less than the solids retention time of the biomass in the process. The secondary famine process may be initiated periodically. As used herein, "periodically" means from time-to-time and after a plurality of primary feast-famine cycles. That is, the secondary famine process need not be initiated based on fixed time intervals. Instead, the time intervals between successive secondary famine processes can vary. In some embodiments, the secondary perturbation occurs at least once every four sludge retention times (SRTs).

The present disclosure is further directed to a process or method for enhancing the PAP of a biomass over and above what may be expected from subjecting the biomass to a fixed cyclic regime of feast and famine conditions. PAP of a biomass may be influenced by two factors. A higher PAP is demonstrated by a biomass enriched with a higher fraction of populations of bacteria with a metabolic capability to convert RBCOD into intracellular stored PHA. A higher PAP may also be due to the physiological state of the biomass at the time of the accumulation process. The feast and famine regime selects for preferred survival of populations of PHA storing bacteria in the biomass. It is hypothesized that the specific conditions of feast and famine, based on time and organic loading, also conditions those PHA storing bacteria to be prepared to not store more PHA than they need to store during feast. Typically in practical conditions of biological treatment processes the level of PHA that is stored is low compared to the ultimate levels desired for the PHA accumulation process. Thus, the methods of the present invention aim to combine conditions of PAP enrichment with conditions that tend to maintain the biomass with an improved physiological state for PHA accumulation. Notwithstanding this interpretation, and the potential for other such interpretations, the present methods provide for augmented process conditions over and above those of the basic feast-famine strategy such that an enhanced performance in PHA accumulation is accomplished.

Other objects and advantages of the present invention will become apparent and obvious from a study of the following description and the accompanying drawings which are merely illustrative of such invention.

DESCRIPTION OF PREFERRED EMBODIMENTS OF THE INVENTION

Figure 1:
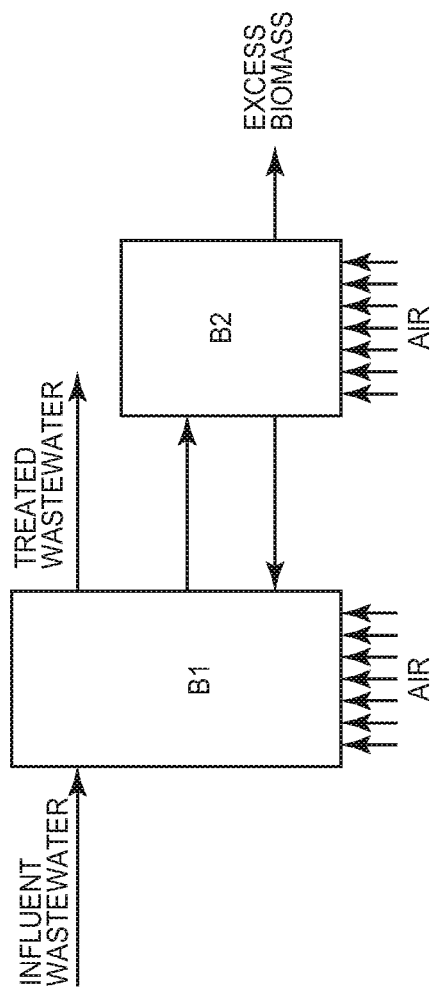
FIG. 1 is a schematic illustration of one embodiment of a semi-continuous flow biological wastewater treatment process that enhances the PHA accumulation potential in biomass employed in the biological process.

The methods discussed herein are based on the finding that biomass coming from famine conditions can be stimulated to exhibit an enhancement in its PHA accumulation potential (PAP) by imposing a secondary perturbation to the repeated cycles of the biomass feast and famine during biological water treatment. In one embodiment, such secondary perturbation may be achieved by exposing the biomass or at least a fraction of the biomass to a periodically applied extended period of famine. Such exposure may occur at a given interval in time.

By preventing the biomass from adapting to a steady monotony of feast-famine cycling, the biomass improves performance by reaching a higher extant PAP when compared to the same biological treatment where the biomass is subjected to a simple fixed cyclic regime of feast and famine. Exposing the biomass, or fractions of the biomass at a given interval in time, to an extended period of famine (sometimes referred to secondary famine) has been found to stimulate enhanced PHA storing potential as compared to the same biomass exposed to just the cyclic regime of feast and famine (sometimes referred to as primary feast and famine conditions) without such periodic intervals of an extended famine. This additional periodically applied period of famine is called a secondary perturbation to the biomass. The primary perturbation to the biomass is the feast and famine cyclic regime.

The secondary perturbation of additional periodic starvation imposed on the biomass over and above the routine regime of famine serves to condition the biomass in order to increase its potential for PHA storage before entering the accumulation stage of the process. In the accumulation stage, in order to extract the highest value from biomass harvested from a biological treatment system, the biomass accumulates PHA preferably to a level near its full expressed potential. The stimulation of an enhanced PAP facilitates greater volumetric productivity during the accumulation process and increases the economy of the PHA recovery from the biomass, since a greater level of PHA accumulation is expressed by the biomass for the same accumulation process.

The PHA storage response in activated sludge treating water (wastewater, process water, etc.) is triggered by availability of RBCOD during feast conditions. Whereas some contaminated water may have high fractions of RBCOD over total COD, other untreated waters, such as for instance municipal wastewaters, are often with lower fractions of RBCOD over total COD. Lower fractions of RBCOD may reduce the ability to produce a biomass with PAP in excess of 50% g-PHA/g-VSS. Here it is of increased need to drive the process such that the full possible extent of PAP is expressed by the biomass during the accumulation process. Therefore, the methods described in this disclosure are of further and particular interest when operating a process for biomass production with PAP using wastewaters with low or moderate fractions of RBCOD over total COD.

The secondary perturbation can be carried out in different ways. Without limitation, several illustrative examples of embodiments are disclosed below in which a biomass or fractions of a biomass from a process may be subjected to an extended starvation period in batch mode, semi-continuous mode, and continuous mode. Two experimental examples illustrate the batch mode (Example 1) and continuous mode (Example 2) embodiments. It is noted that in some embodiments, a secondary perturbation of famine may be applied after the biomass is subjected to at least two cycles of feast-famine.

Notwithstanding the possibility for other analogous process flow schemes that may similarly impose a secondary perturbation on the biomass, the methods described herein that incorporate a secondary famine process with primary feast and famine selection may be summarized based on the experimental results as follows:
A method or process where a biomass is subjected to repeated cycles of feast and famine wherein the biomass, or fractions of the process biomass, is subjected to a period of extended famine such that:
  The period of extended famine for the biomass or fractions of the biomass at any given time is less than or equal to 1 solids retention time (SRT),
  The length of a secondary (famine) perturbation for the biomass or fractions of the biomass is statistically greater than the average famine period in primary feast-famine cycles and at least equal to the average primary feast-famine period, and
  The given interval in time between repeated secondary perturbation events may vary for the biomass, or fractions of the biomass at any given time, but it is at least as frequently as once every 4 SRTs.
Note that by conventional definition, the SRT is the total mass inventory of biomass divided by the average mass flux of biomass exported from the process. In typical operation of activated sludge processes treating COD in wastewater, SRTs of between 2 to 6 days are often applied. Therefore, in absence of defining the SRT for the process, a practical operational limit for the length of the period of extended famine for the biomass or fractions of the biomass at any given time is less than or equal to 6 days.

ILLUSTRATIVE EXAMPLES OF PROCESS EMBODIMENTS

Subjecting the Biomass to Secondary Famine Conditions or Famine Perturbation at a Given Interval of Time In one embodiment, the method is carried out under a batch operation mode. In this embodiment, the process biomass that has been enriched under feast and famine conditions is subjected as a whole to an extended phase of famine. This extended famine phase may be brought about by preventing organic substrate from being supplied to the biomass during this period. An example of such a process is demonstrated in Example 1, below.

Subjecting Fractions of the Biomass to Secondary Famine Conditions or Secondary Perturbation at a Given Interval of Time FIG. 1 depicts another embodiment of the method. This embodiment is carried out under continuous or semi-continuous operating conditions rather than in the batch operation mode described in Example 1.

In this embodiment, the secondary perturbation imposed on the biomass occurs in a separate reactor. Not all the biomass is exposed to the secondary perturbation at the same time. However, on average, substantially all the microorganisms in the biomass see a similar periodicity and duration of secondary perturbation.

In one embodiment, the reactor where the secondary perturbation is carried out is placed in a sidestream line separated from a mainstream water treatment line. As depicted in FIG. 1, the perturbation reactor (B2, sometimes referred to as a secondary famine reactor) is connected to the mainstream reactor, in this case an SBR (B1). Mixed liquor is pumped from the mainstream reactor (B1) to the second reactor (B2) at selected intervals. In a preferred embodiment, the biomass in reactor (B1) is in the phase of famine at the time of biomass being pumped to the second reactor (B2) from B1. The retention time of the biomass in the second reactor (B2) is controlled so as to cause a secondary perturbation on the biomass. This stimulates an enhancement in the PAP of the biomass when compared to PAP of the biomass without benefit of reactor (B2) but with the same feast and famine regime that is established by the operation of reactor (B1).

A Sequencing Batch Reactor with a Sidestream Secondary Famine Reactor

In the embodiment depicted in FIG. 1, the secondary perturbation reactor (B2) is operating semi-continuously mutually with a mainstream SBR. The operation sequence of an SBR cycle may be as follows:
  1. Mixed liquor containing biomass from the previous cycle is conveyed from (B2) to (B1).
  2. Wastewater is fed to the reactor (B1).
  3. Feast conditions are imposed to the biomass in (B1). Feast may be with aerobic, anoxic, or anaerobic conditions maintained.
  4. The RBCOD in the mixed liquor is exhausted and, thus, primary famine conditions are then imposed on the biomass in reactor (B1).
  5. During the primary famine phase, mixed liquor is pumped from the mainstream reactor (B1) to the secondary perturbation reactor (B2).
  6. Surplus biomass is removed (harvested) from the system (from B1 or B2) and thereafter exploited for PHA production.
  7. After a sufficient duration of primary famine in the mainstream reactor (B1), quiescent conditions are established allowing the biomass to settle.
  8. The supernatant of clarified (treated) water is discharged.
  9. The SBR cycle is repeated.
In this embodiment the process is characterized by:
  The primary feast and famine conditions selects a biomass with PHA accumulation potential (PAP) and is carried out in a mainstream biological treatment reactor (such as, for example, an SBR).

Fractions of the biomass are moved from the mainstream to the sidestream reactor. These biomass fractions are subjected to famine conditions in the sidestream reactor.

Fractions of the biomass disposed to the sidestream reactor are subjected to a secondary perturbation of famine by virtue of an extended period of starvation while in the sidestream reactor.

The average duration for the secondary perturbation is controlled by the volumes and interval of exchange of mixed liquor containing biomass to and from the main and sidestream reactors.

The biomass SRT in the overall process (including all reactor volumes) is controlled by exporting (harvesting) biomass from the mainstream and/or the sidestream reactors.

Harvested biomass may be directed to an accumulation process.

The average retention time (representing the period of secondary famine) of the biomass in the sidestream reactor is longer than the average famine duration in the mainstream reactor but shorter than the SRT of the biomass in the overall process.

The secondary famine or perturbation conditions for the biomass are such that when the harvested biomass is made to accumulate PHA, the PAP is higher compared to a biomass that is operating under the same regime of feast and famine in reactor (B1) and exclusive of reactor (B2) and any other form of secondary perturbation.

A Continuous Flow System with a Sidestream Secondary Famine Reactor

Figure 2:
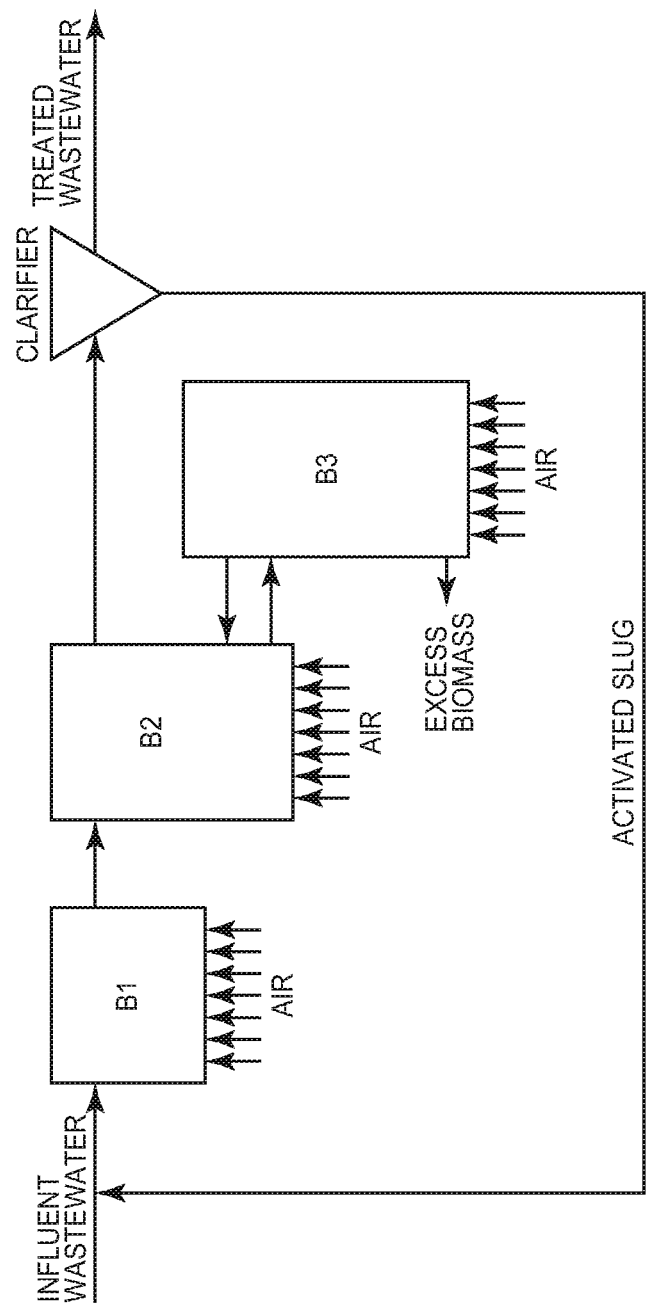
FIG. 2 is a schematic illustration of one embodiment of a continuous flow biological wastewater treatment process that enhances the PHA accumulation potential in biomass employed in the biological process.

In another embodiment, primary feast and famine conditions are carried out under a continuous flow wastewater treatment process design. Rather than employing a sequencing batch reactor, such as the one disclosed in FIG. 1, reactors in series are employed so that feast conditions are carried out in a feast reactor (B1) followed by a primary famine reactor (B2). One example of a system that may be utilized with such an embodiment is shown in FIG. 2. In the FIG. 2 system, the secondary famine conditions are carried out by moving biomass from the primary famine reactor (B2) to the secondary famine reactor (B3) that is located in a sidestream relative to the feast reactor (B1) and the primary famine reactor (B2).

Figure 3:
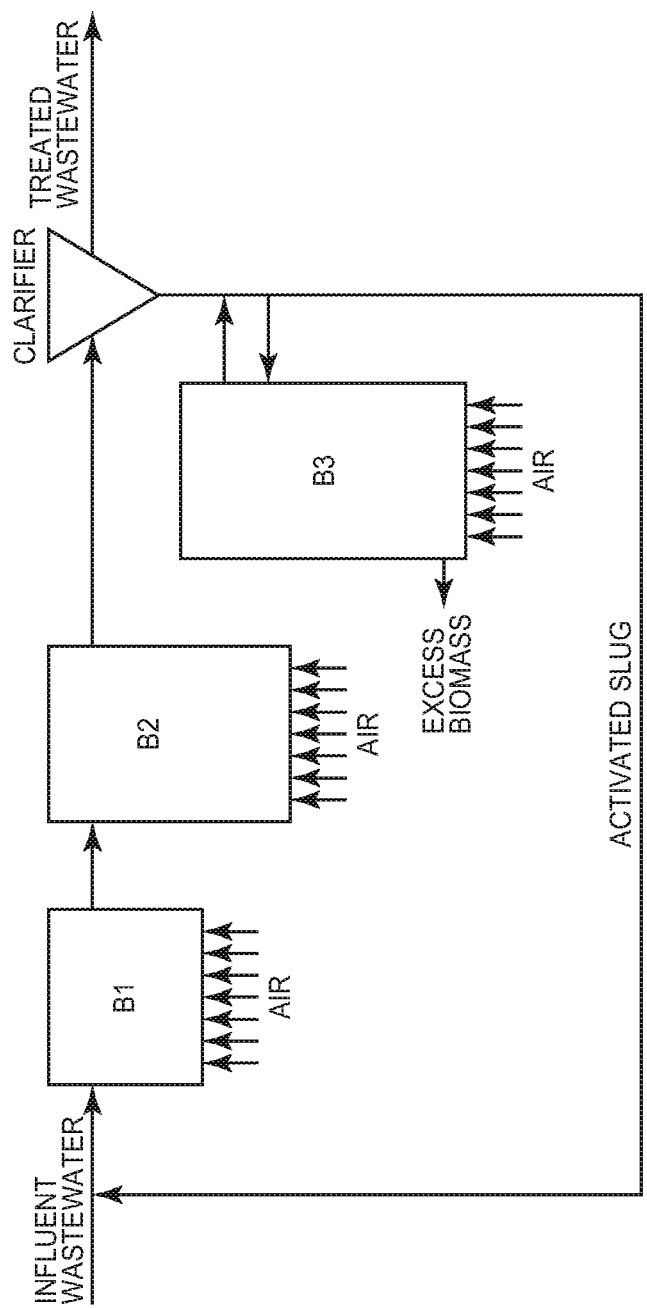
FIG. 3 is a schematic illustration of another embodiment of a continuous flow biological wastewater treatment process that enhances the PHA accumulation potential in biomass employed in the biological process.

Another embodiment is illustrated in the process shown in FIG. 3. In this embodiment, secondary famine treatment may be achieved off the return activated sludge line that leads biomass separated from a clarifier after primary famine back to primary feast located upstream in the mainstream.

Figure 4:
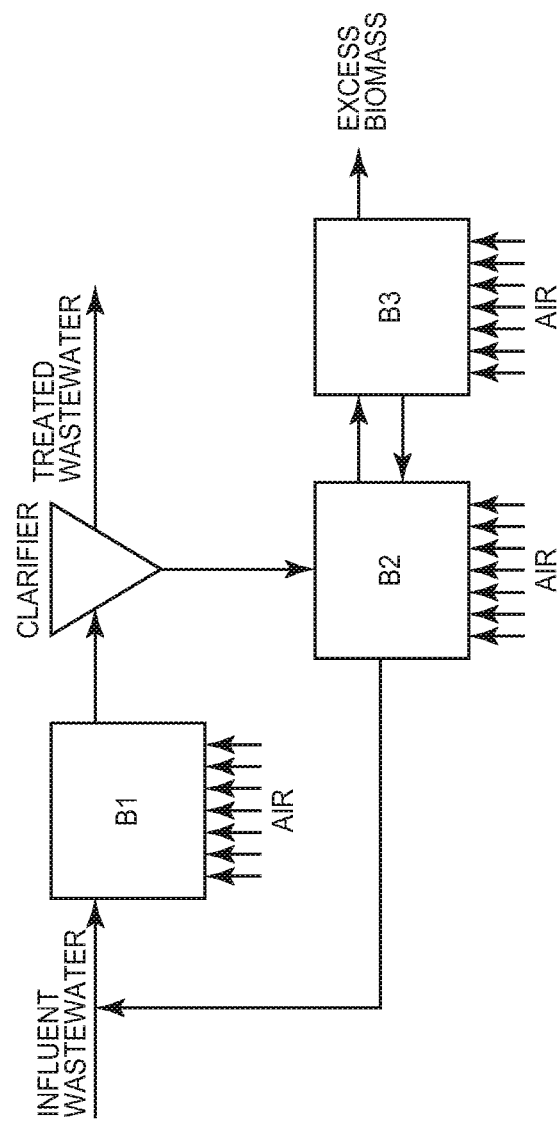
FIG. 4 is a schematic illustration of another embodiment of a continuous flow biological wastewater treatment process that enhances the PHA accumulation potential in biomass employed in the biological process.

Another embodiment is illustrated in the process shown in FIG. 4. In this embodiment, primary famine (B2) as well as secondary famine (B3) treatment may be achieved in sidestream reactors.

In another embodiment, primary famine may be initiated in the mainstream and completed in a sidestream reactor that is integrated with the return activated sludge line. Thus, the primary famine reactor volume providing the time of exposure to primary famine conditions may be split between the mainstream and sidestream. The secondary famine reactor can be located off the sidestream primary famine reactor or off the return activated sludge line.

In yet another embodiment, reactors B1 and B2 may be established as part of a single or multiple of reactor volumes that create for more plug flow hydraulic conditions.

In general, it may be said that times of primary feast and primary famine may be delineated by the process hydraulic conditions and the time those hydraulic conditions provide for periods of high (feast) and relatively low (famine) respiration rates for the biomass. Similarly, the process hydraulics and the time those hydraulic conditions provide for an intermittent period of extended (secondary) famine establish the effect of a secondary perturbation for reaching an enhanced PAP.

In the embodiments illustrated by FIGS. 2, 3, and 4, the processes may be generally characterized by:

Influent RBCOD containing water is used to stimulate the biomass to primary feast conditions.

A downstream famine reactor or zone establishes primary famine conditions due to consumption of RBCOD in the feast reactor.

Selection of biomass with PAP is by virtue of an imposed cyclic regime of primary feast and famine conditions.

Fractions of the biomass at any given time are moved from conditions of primary famine to conditions of a secondary famine (or secondary perturbation) by virtue of periodically being exposed to prolonged starvation conditions.

Biomass after being disposed to a secondary perturbation of famine can be moved back to conditions of cyclic primary feast and famine conditions.

The retention time of the biomass in conditions of secondary perturbation is on average longer than the duration of famine in the mainstream (and or sidestream) but shorter than the overall biomass SRT in the process.

Secondary perturbation conditions for the biomass are such that when the biomass is made to accumulate PHA, the PAP is higher compared to biomass in the same process that has only been exposed to the primary feast and famine perturbation.

Method of Biologically Removing Nitrogen from a Wastewater Stream and Enhancing the PHA Accumulation Potential of Biomass Including a Secondary Famine or, So-called, Secondary Perturbation Process Municipal wastewater typically contains levels of nitrogen that are in excess of biomass requirements for growth based on the influent organic matter. Therefore, nitrification and denitrification unit processes are frequently integrated to organic carbon removal in the bioprocess design for municipal wastewater treatment. Thus, some embodiments of the present invention allow for treatment of wastewater and production of biomass with PAP under feast and famine conditions with secondary perturbation, as well as meeting water quality objectives of nitrogen removal. That is, removal of organic matter, as well as nitrogen, from the wastewater is achieved with the added value of harvesting a biomass with enhanced PAP.

Figure 5:
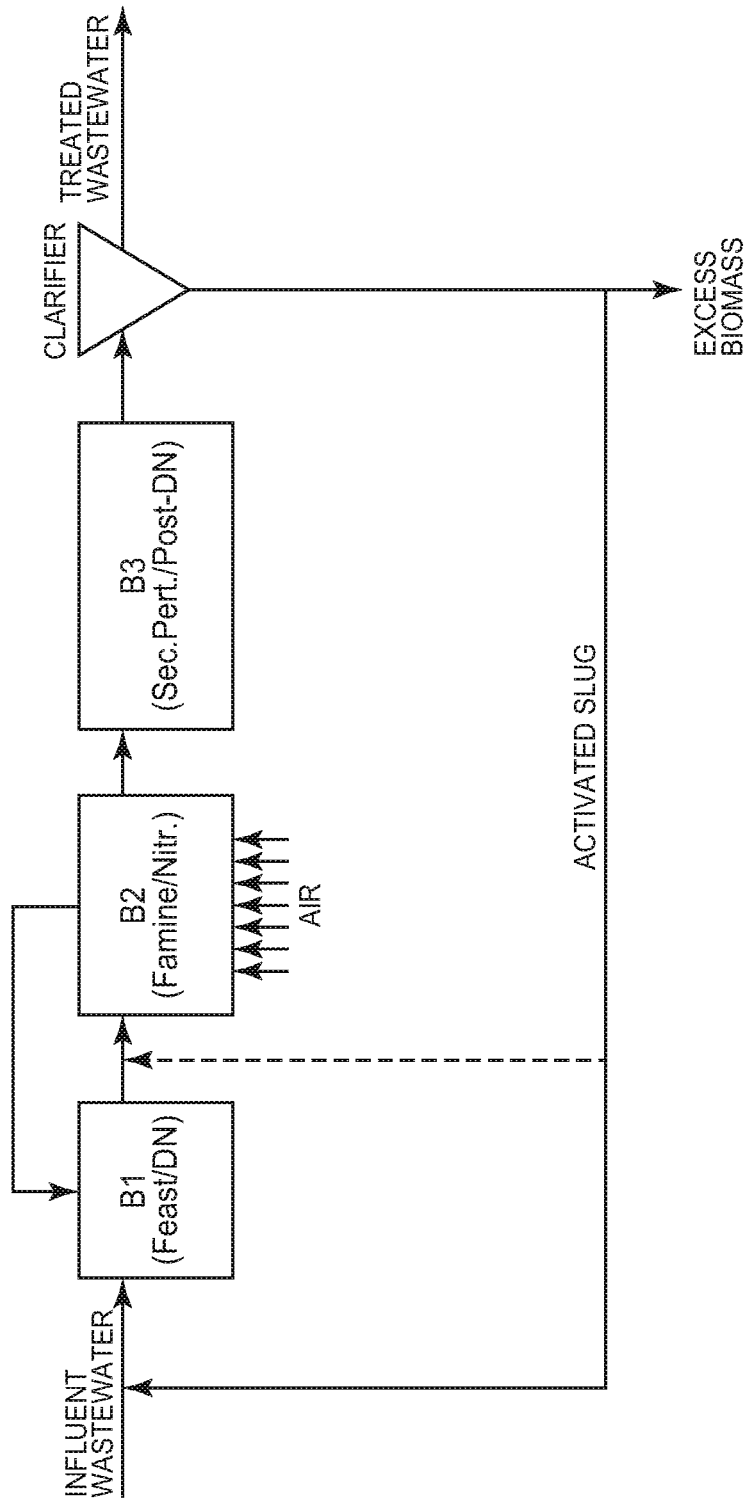
FIG. 5 is a schematic illustration of a biological wastewater treatment process designed to nitrify and denitrify wastewater and, at the same time, enhance the PHA accumulation potential in biomass employed in the process.

FIG. 5 shows a process for producing a PAP-enriched biomass with secondary famine or perturbation in combination with a nitrogen removal process. Here, there are two anoxic reactors, reactor (B1) and reactor (B3). Both are mixed by means of mechanical agitation. Denitrification (DN) is performed in reactor (B1). Also, primary perturbation, that is primary feast and primary famine conditions are maintained in reactor (B1) and reactor (B2), respectively. Secondary famine or perturbation (Sec. Pert.) is carried out in a secondary famine reactor (B3). In embodiments emphasizing carbon removal, reactor (B1) and reactor (B3) may be maintained under aerobic conditions.

Turning to FIG. 5 in detail, influent wastewater, preferably after some form of primary treatment, is directed to a first reactor (B1) where the biomass is stimulated into feast by the influent RBCOD and under anoxic conditions (i.e.

with nitrate or nitrite as electron acceptor). Thereafter, the mixed liquor is directed to an aerated reactor (B2) in which nitrification ensues.

Nitrification activity may be sustained by populations of nitrifying microorganisms in the suspended solids. Alternatively, the populations of nitrifying microorganisms may be more robustly maintained by the application of an integrated biofilm activated sludge (IFAS) unit process design. In such an integrated biofilm activated sludge (IFAS) process, the biofilm biomass may, due to distinctions in retention time, serve to facilitate ammonia-nitrogen removal and/or non-RBCOD degradation. An example of an IFAS process that may be used with the methods described herein is one where an activated sludge is integrated with a moving bed biofilm reactor (MBBR) biofilm process, such as the Hybas™ process from AnoxKaldnes, headquartered in Lund, Sweden. In the case of an IFAS process, the SRT for the purposes of considering secondary perturbation is the SRT based on just the biomass fraction represented by the suspended solids in the process.

During the period of nitrification, the populations of heterotrophic bacteria in the activated sludge biomass coming from the anoxic feast reactor (B1) will be subjected to famine conditions due to a lack of RBCOD.

A portion of mixed liquor is recirculated from (B2) to (B1) in order to make nitrate available for the anoxic feast conditions imposed in (B1). Therefore, the recirculation of mixed liquor between (B1) and (B2) plays a part in creating feast and primary famine conditions in reactors (B1) and (B2).

Mixed liquor is otherwise directed from (B2) to (B3). Reactor (B3) provides for secondary perturbation of periodic extended famine of the heterotrophic bacteria in the biomass. A prolonged period of famine is introduced in (B3) over and above the regime of routine or primary famine experienced by the biomass in (B2). In this embodiment, secondary perturbation is applied under anoxic conditions with nitrate or nitrite as the electron acceptor. The secondary perturbation, therefore, serves simultaneously as a post-denitrification stage for nitrogen effluent water quality management. Since no additional RBCOD is supplied to this stage, the post-denitrification is intended to be driven by endogenous respiration in the biomass.

Following post-denitrification in (B3), the suspended biomass is maintained in the process by gravity settling. The return activated sludge may be directed to either reactor (B1) or reactor (B2). Thus, control of the primary feast-famine cycle lengths and the length and frequency of secondary perturbation may be made by selecting the fraction of the return activated sludge directed to (B1) or (B2), as well as by adjusting the internal recirculation flow between (B1) and (B2).

The embodiments illustrated in FIG. 5, may be summarized by:
Influent wastewater directed into a feast reactor (B1) in which the biomass is subjected to anoxic feast conditions.
An aerated downstream famine reactor (B2) in which the heterotrophic fraction of the biomass enters famine conditions.
Autotrophic bacteria convert influent wastewater ammonia-nitrogen to nitrate or nitrite in the aerated downstream famine reactor (B2).
Mixed liquor is recirculated between the famine/nitrification reactor (B2) and the anoxic feast reactor (B1).
Selection of biomass with PAP is accomplished by virtue of directing the heterotrophic fraction of the biomass to primary perturbation of anoxic feast and aerobic famine accomplished in the first two reactors, reactor (B1) and reactor (B2).
Mixed liquor from the famine/nitrification reactor (B2) is directed to the secondary famine or perturbation reactor (B3) and the biomass therein is subjected to the secondary starvation conditions due to a lack of RBCOD. Secondary famine or perturbation occurs under anoxic conditions serving the additional function of nitrogen removal from the water.
Biomass from secondary perturbation is recycled to the primary famine and/or feast reactor.
The average retention time of the biomass in the secondary perturbation reactor is longer than the average duration of famine in the mainstream but shorter than the global SRT for the suspended solids in the system.
Secondary perturbation conditions for the biomass are such that, when the biomass is made to accumulate PHA, the PAP is enhanced compared to a biomass produced on the same primary feast-famine perturbation exclusive of any form of secondary perturbation.

In the embodiments illustrated by FIG. 5, preferred embodiments are such that:
The average flow rate of biomass from the clarifier to (B1) or (B2) is between 0.2 and 2 times the average flow rate of influent wastewater to the process.
The average flow rate of mixed liquor from (B2) to (B1) is between 1 and 5 times the average flow rate of influent wastewater to the process.

In absence of the requirement to treat nitrogen, the flow scheme shown in FIG. 5 could be applied to achieve secondary perturbation in continuous flow and for carbon removal only. In this case, (B1) and (B3) would both be aerated and maintained as aerobic reactors.

EXAMPLE 1

Stimulating Enhanced PHA Accumulation Potential by Secondary Perturbation of Famine in Batch Mode Two laboratory scale reactors were operated in parallel under well-controlled conditions of the biomass history. In one of the reactors, a secondary perturbation was imposed on all the process biomass at the same time. A significantly enhanced potential to accumulate PHA was observed in biomass from this reactor in comparison to the experimental control.

Methods and Materials

A process according to the preferred embodiment was carried out in laboratory scale systems. Municipal wastewater was treated by activated sludge. The biomass was produced under operating conditions of feast and famine in order to enrich for PHA-storage potential, as has been previously disclosed (WO 2012/023114A1). The activated sludge treatment was in two 4 L sequencing batch reactors (SBRs) operating in parallel. The SBRs were closely monitored by means of on-line measurements with dissolved oxygen and pH probes.

The SBRs were fed with domestic wastewater obtained directly from a sewer system that serves 150 European communities. The sewer delivers 1.7 million $m^3$/day of raw, untreated, domestic wastewater. The domestic wastewater drawn from the sewer was filtered (primary treatment) in order to remove suspended solids before being biologically treated in the SBRs. The primary treated wastewater composition was on average 748 mg-COD/L of total COD, 196 mg-COD/L of soluble COD, 32.2 mg-N/L of total soluble nitrogen, and 3.31 mg-P/L of total soluble phosphorus.

One of the SBRs was inoculated with activated sludge from the Brussels North full-scale wastewater treatment plant and operated according to the conditions described below. After 140 days of operation of this SBR (SBR-A), the SBR was duplicated by seeding the biomass produced from SBR-A into a second identical SBR (SBR-B). This seeding was conducted by continuously collecting the excess activated sludge produced twice per day in SBR-A over the course of 4 days and storing the biomass at 4° C. After these 4 days of collection, the biomass from SBR-A was well-mixed with the biomass stored in the refrigerator and then divided equally between the two SBRs (SBR-A and SBR-B) as a means to ensure identical initial conditions of biomass history for the planned experiment with SBRs A and B. SBR-A was the experimental control.

The operating conditions of SBRs A and B were identical except for one period when all the biomass of SBR-B was subjected to a secondary perturbation in the form of a prolonged famine lasting for four days. During this secondary perturbation of extended famine the biomass was maintained with only mixing and aeration.

Notwithstanding the perturbation of extended famine for the biomass of SBR-B, the SBRs treated primary effluent at 20° C. while applying repeated cycles of primary (feast and famine) perturbation. Each operating feast-famine cycle comprised rapidly feeding the SBRs with 3 L of primary treated domestic wastewater for feast stimulation (over a 10 min period) and then aerating for 40 min to reach conditions of famine. At the end of the aerated reaction phase, 50 ml of mixed liquor was wasted in 1 minute (waste activated sludge production). Subsequently, activated sludge was settled (no mixing or aeration) for 26 min. Effluent supernatant could then be rapidly discharged over 3 minutes, leaving 1 L mixed liquor before starting the next in the regime of 18 feast and famine SBR cycles per day.

With these operating conditions, the total hydraulic retention time (HRT) was 1.8 h, whereby the HRT with respect to aerobic conditions was 0.9 h. Similarly, the sludge retention time (SRT) was 1.8 days, while the aerobic SRT was 0.9 days. SRT takes into account waste sludge production and suspended solids lost in the effluent discharge.

The PHA accumulation potential (PAP) in the activated sludge biomass was assessed according to a reference method. Biomass grab samples were harvested from the SBRs at the end of famine just before the settling stage, transferred to batch reactors, and diluted with tap water to nominally 0.5 g-VSS/L. Two well-mixed 10 L fed batch reactors were operated in parallel aerobically for 24 hours at 20° C. with 4 L mixed liquor volumes. Standardized feeding was used for all batch experiments. Feeding for PHA accumulation was achieved by two pulse-additions of a concentrated sodium acetate solution, each providing an increase in acetate concentration in the reactor of 1 g-COD/L. The aliquots of added acetate were provided at the start of each accumulation experiment (0 h) and after six hours (6 h). No supplementary nutrients were added, such that the only nutrients present in the accumulation reactor mixed liquor were those carried over from the SBR grab sample. Each accumulation was carried out for about 24 h. The pH was not controlled automatically; however, a pH adjustment was applied as necessary by addition of $H_2SO_4$ along with the substrate addition in order to maintain pH under 8.5.

The accumulation trends were monitored by sampling the fed-batch reactors at selected times over the 24 hours. Samples were centrifuged (10 min at 4000 rpm), followed by filtration (0.45 μm pore size), for soluble COD measurement. The remaining biomass pellet was dried overnight at 105° C. and digested in order to assess the biomass PHA content by GCMS (See Werker A, Lind P, Bengtsson S, Nordström F, 2008. Chlorinated-solvent-free gas chromatographic analysis of biomass containing polyhydroxyalkanoates. Water Research 42:2517-2526).

The trend of PHA accumulation over time was fit by least squares regression analysis to an empirical function of form:

$$PAP_t = A_0 + A_e(1 - exp(-kt)) \quad \text{(Equation 1)}$$

where, $PAP_t$=the PHA accumulation Potential referenced to t-hours of accumulation $A_0$=an empirical constant estimating initial PHA content or $PAP_0$ $A_e$=an empirical constant of the extrapolated PHA accumulation capacity k=a rate constant ($h^{-1}$) estimating the rate of the PHA accumulation Results and Discussion After only a few days of SBR operation, a pattern of respiration based on dissolved oxygen (DO) trends typical for a stable feast and famine biomass response was observed. Feast conditions occurred upon wastewater feeding and were associated with elevated respiration rates evidenced by a lower corresponding DO concentration. Once the RBCOD fed with the influent wastewater was consumed, the activated sludge became exposed to famine conditions associated with lower respiration rates marked as a transition from feast by a sudden increase in DO concentration. The ratio of the duration of feast to the total aerobic time is known to reflect the selection pressure towards enrichment for PAP. A low ratio generally indicates a strong selective pressure. For SBR-A, the ratio of feast to total aerobic time decreased to 0.25 over the course of the first 21 days of operation. After about 90 days of operation and following an adjustment to improve the reactor aeration, the feast to total aerobic time ratio settled to a lower value of 0.17.

The removal of influent COD was on average 70% throughout the operation period. Approximately 88% of the influent soluble COD (SCOD) was consumed during the feast period. The combination of a low feast to the aerobic (feast-famine) time ratio and a high fraction of SCOD consumed during feast were indicators of a good, stable (primary) feast and famine selection pressure and response of the SBR biomass.

The PHA accumulation potential of the activated sludge in SBR-A, as determined by the reference assessment method, increased substantially over the course of the reactor operation. The original activated sludge used to inoculate the reactor exhibited a $PAP_{24}$ of about 9% (g-PHA/g-VSS). After 16 days of enrichment in SBR-A, the biomass $PAP_6$ and $PAP_{24}$ were about 20% and 47% g-PHA/g-VSS, respectively. This range of PAP was sustained in 5 replicate assessments over the 140 days of operation with $PAP_6$ between 13 and 26% and $PAP_{24}$ between 31 and 47% g-PHA/g-VSS.

After 140 days of operation of SBR-A, the excess biomass produced in the system was used to inoculate a second SBR (SBR-B) as described above. After mixing the stored excess biomass (4 L) with the biomass in SBR-A (4 L) and inoculating both SBRs by splitting these 8 L of mixed liquor, SBR-A was continuously operated under the same conditions as before.

Two days after the reinoculation of the two SBRs, SBR-B was subjected to a famine perturbation of four days. After this perturbation, normal SBR operating conditions were resumed. SBR-A was continuously operated as before with just the primary feast-famine perturbation, making SBR-A an experimental control. The influence of the imposed starvation period on PAP was similarly evaluated by the reference PAP assessment method. These tests were carried out one day after the reinoculation of the SBRs (day 1), after the starvation period (day 7), at 4 days after the starvation (day 10), 11 days after the starvation (day 17) and 18 days after the starvation (day 24).

It should be noted that due to the manner of the parallel SBR-A and B restart after 140 days of SBR-A operation, the fraction of the inoculation biomass that was stored was also subjected to starvation conditions albeit in refrigerated storage. Since some of the biomass was stored during the four days of collection, the fraction of the starting biomass culture divided to both SBRs were perturbed from the initial steady state primary perturbation conditions established for producing the biomass in SBR-A. Notwithstanding, SBR-B biomass was exposed to a more stringent perturbation of famine with aeration at 20° C. for 4 days.

Figure 6:
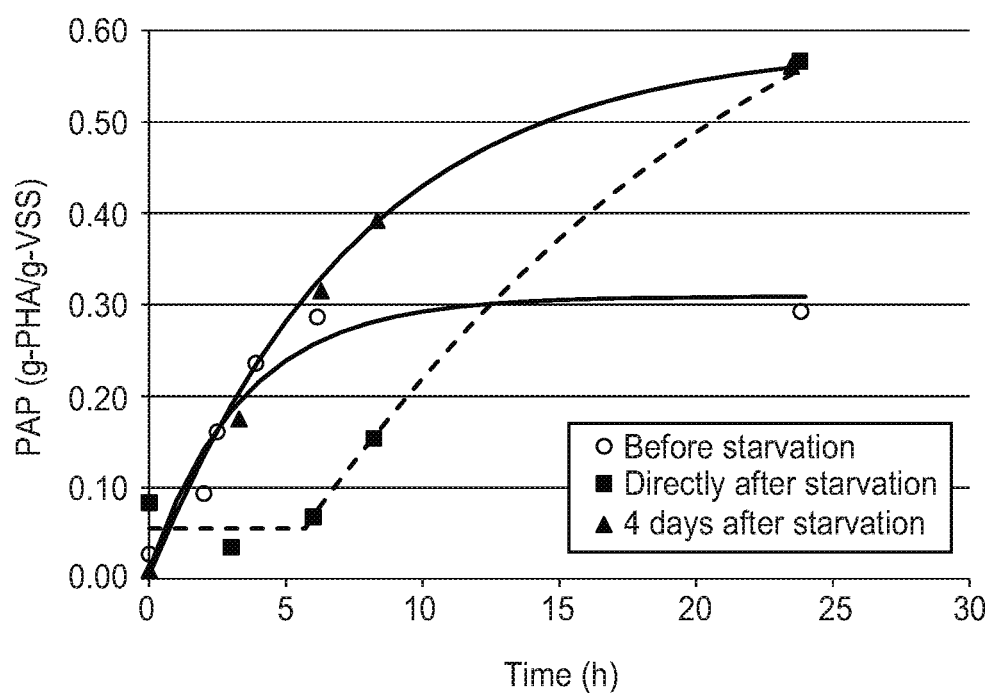
FIG. 6 is a graphical illustration of PHA accumulation potential for biomass produced in a sequencing batch reactor process at various times relative to the imposed secondary famine conditions.

The secondary perturbation imposed on SBR-B biomass stimulated an enhancement on the biomass PAP with respect to the control SBR-A (FIG. 6). Although the PAP measured directly after the starvation period was with a prolonged lag phase of 6 hours, the subsequent PHA accumulation kicked off at a high rate and reached 57% g-PHA/g-VSS at 24 h. The accumulation carried out around one SRT after the starvation period (day 10) showed a pronounced increase in PAP compared to the control reactor at both 6 h (32% g-PHA/g-VSS) and at 24 h (56% g-PHA/g-VSS) of accumulation.

Figure 7:
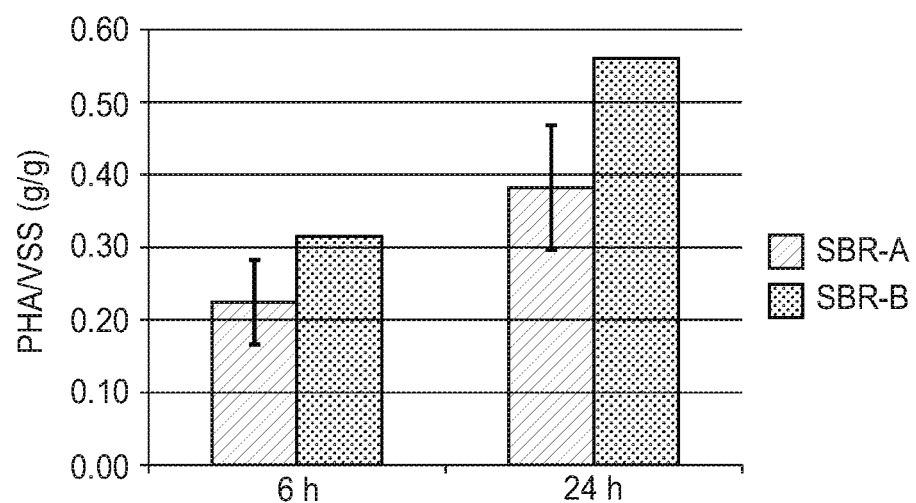
FIG. 7 is a graphical illustration of PHA accumulation potential for biomass that has been exposed to secondary famine conditions compared to PHA accumulation potential for a biomass that has only been exposed to primary feast and famine conditions.
Figure 8:
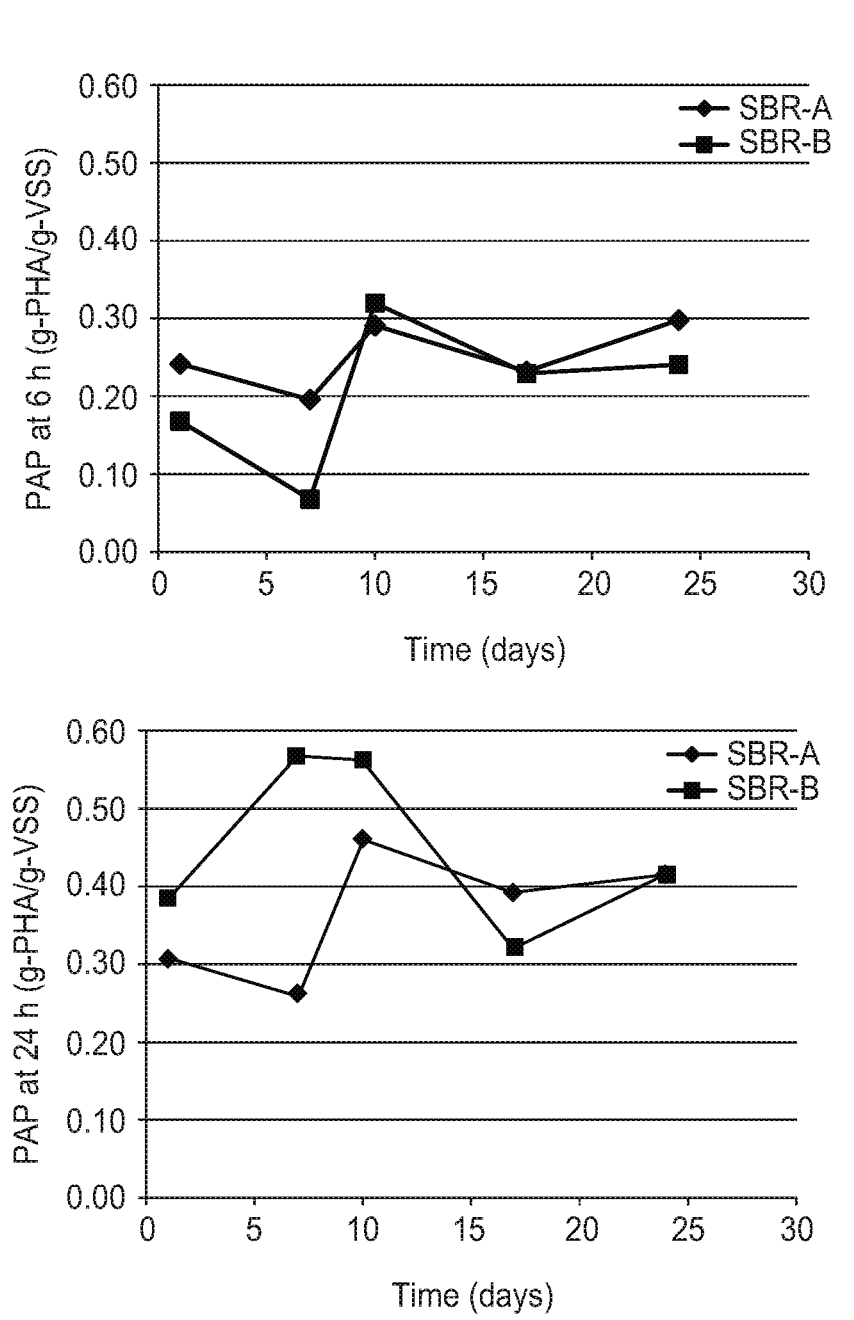
FIG. 8 is a pair of graphical illustrations showing PHA accumulation potential after six and 24 hours for two processes, one employing secondary famine conditions and the other only employing primary feast and famine conditions.

Relative to the average PAP for the control (SBR-A) over the operational period, the PAP for SBR-B on this occasion was higher by 41% and 47% at 6 and 24 h, respectively. The secondary perturbation stimulated a response that was outside the statistically defined performance range for the control experiment, SBR-A (FIG. 7). PAP for the two reactors is depicted in FIG. 8. The PAP measured in the control reactor (SBR-A) in the period was consistent with what had been previously observed during the initial 140 days. However, a slight increase in PAP for SBR-A was nevertheless noted and attributed to the history of biomass starvation imparted as part of the collection and refrigerated storage of biomass prior to the reinoculation as detailed above.

In conclusion, we found that an imposed controlled secondary perturbation in the form of a periodically applied extended famine that was otherwise longer than the cycle time of famine in primary perturbation of feast-famine selection and less than the SRT of the biomass contributed significantly towards enhancing PHA accumulation performance relative to a steady state regime of only repeated cycles of primary (feast and famine) perturbation.

EXAMPLE 2

Stimulating Enhanced PHA Accumulation Potential in Biomass by Subjecting the Biomass to Secondary Famine Conditions in Sequencing Batch Operation Two laboratory scale sequencing batch reactors (SBRs) were operated in parallel. One of the SBRs was connected to a secondary famine reactor (sometimes the secondary famine reactor is referred to as a secondary perturbation reactor) in which famine was imposed on at least a portion of the biomass as part of the operational cycle of the system. In this way, significantly enhanced potential to accumulate PHA was generated compared to the control reactor, which was operated with the same primary (feast-famine) perturbation but without any secondary perturbation.

Methods and Materials

A process according to a preferred embodiment was carried out in laboratory scale activated sludge systems. Two SBRs were operated in parallel under operating conditions of primary (feast and famine) perturbation in order to enrich the biomass for PHA-accumulation potential (PAP). The conditions were similar to the ones used in Example 1 and the same source of municipal wastewater was employed.

One of SBRs (SBR-A) served as an experimental control reactor with a working volume of 6 L. The other SBR (SBR-(B1)) was with identical operating conditions except that it was operated in tandem with a sidestream secondary perturbation reactor (B2) according to the principles outlined above and depicted in FIG. 1. The secondary perturbation reactor had a working volume 1.8 L. Both SBR-A and SBR-(B1) were closely monitored by means of on-line measurements with dissolved oxygen and pH probes.

Each operating cycle of SBR-(B1) with (B2) contained the following stages:

| | | |
|---|---|---|
| 1. | Feeding of influent wastewater (4.5 L) | 7 minutes |
| 2. | Aerated reaction phase including feast and famine conditions | 40 minutes |
| 3. | Discharge of waste activated sludge (WAS) from (B2) (100 mL) | 1 minute |
| 4. | Transfer of mixed liquor from (B1) to (B2) (150 mL) | 2 minutes |
| 5. | Transfer of mixed liquor from (B2) to (B1) (50 mL) | 2 minutes |
| 6. | Settling of the mixed liquor in (B1) | 25 minutes |
| 7. | Decanting of treated wastewater from (B1) (4.4 L) | 3 minutes |

The biomass in SBR-(B1) was aerated and stirred at all stages except settling and decanting. The reactor (B2) was aerated and stirred at all stages. After decanting the treated wastewater, 1.5 L of mixed liquor was left in the SBR-(B1) before starting the next cycle of 18 cycles per day. These operating conditions resulted in a HRT of 16 h in reactor (B2).

The experimental control SBR (SBR-A) was operated in an identical cycle as SBR-(B1) but without any secondary perturbation reactor. Thus, stages 4 and 5 were omitted in SBR-A. Further, 77 mL of WAS was harvested from SBR-A after famine at every cycle. Consequently, SBR-A was operated under the same volumetric organic loading rate as SBR-(B1). The same solids retention time, based on WAS withdrawal, (4.3-4.8 days) was targeted for the biomass in SBR-A as the biomass in SBR-(B1) with (B2).

The reactors were inoculated by a mixture (50:50 vol-%) of activated sludge from the Brussels North full-scale wastewater treatment plant and activated sludge from a previous laboratory investigation where a mixture of domestic wastewater and a wet-oxidation liquid had been previously used to feed an SBR operated under feast and famine conditions.

The PHA accumulation potential (PAP) in the activated sludge biomass was assessed according to a reference method based on feed-on-demand supply of substrate. Biomass grab samples were harvested from the SBRs at the end of famine just before the settling stage, and then transferred to parallel batch reactors and diluted with tap water to nominally 0.5 g-VSS/L. Two 10 L well-mixed fed batch reactors were operated aerobically for 24-29 hours at 20° C.

with 4 L mixed liquor volumes. A feed-on-demand strategy was used to dose pulses of nominally 200 mg-COD/L based on the respirometric response of the biomass (WO 2011/070544A2). In some experiments, a slightly modified assessment method was used as further detailed below. The reference substrate for PHA accumulation was sodium acetate (100 g/L) with limited levels of N and P added to provide a COD:N:P ratio of 100:1:0.05 (mass basis).

The accumulation trends were monitored by sampling the fed-batch reactors over time in the same way as in Example 1. The trend of PHA accumulation over time was fit by least squares regression analysis to Equation 1 and the estimated function parameters were used in order to compare the performance in accumulation kinetics and the biomass PAP.

Results and Discussion

After start-up of the SBRs, typical patterns of biomass feast and famine respiration based on dissolved oxygen trends were similarly observed for both SBRs. The ratio of the duration of primary feast to the total aerobic primary feast-famine cycle time decreased after an initial acclimation phase to around 0.15 h/h for both the control SBR-A and SBR-(B1). Such values are known to be indicative of a strong selection pressure towards enrichment for PAP.

The concentrations of biomass were, on average, 2.9 and 2.6 g-VSS/L in SBR-A and SBR-(B1), respectively. The removal of influent COD was on average 51% and 47% for SBR-A and SBR-(B1), respectively, with respect to the total COD and 58% and 53% with respect to the soluble COD. The yield of biomass (0.4 g-VSS per g-SCOD removed) was within the range of values that may be typically observed for an activated sludge process that is operated with a relatively short SRT.

Overall the operational performance and the feast and famine responses of SBR-A and SBR-(B1) were similar to one another and similar to what was also observed for the control reactor in Example 1.

The PAP of the biomass from the control SBR (SBR-A) and the SBR operated with inclusion of a secondary perturbation reactor (SBR-(B1)) were evaluated twice each using the reference assessment method based on feed-on-demand supply of a solution of synthetic substrate. The biomass from the control SBR (SBR-A) was assessed at days 4 and 25 of operation whereas the biomass from SBR-(B1) was assessed at days 10 and 53 of operation.

Figure 9:
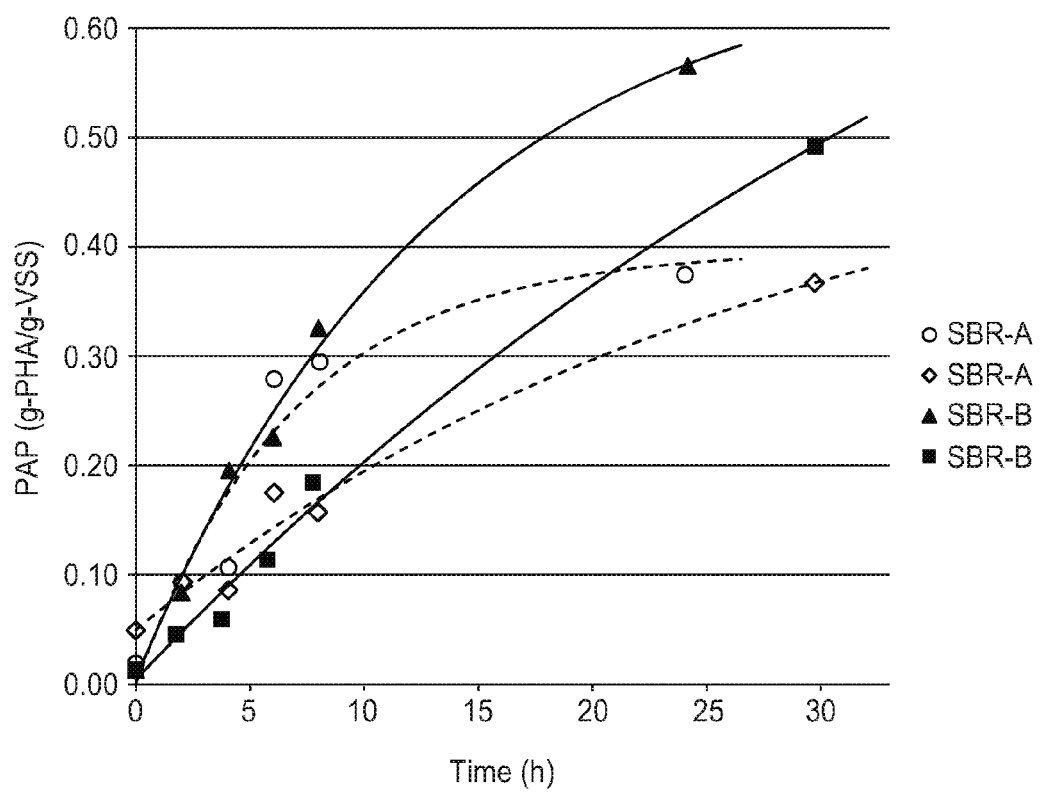
FIG. 9 is another graphical illustration showing PHA accumulation potential for two parallel processes, one in which the biomass is subjected to secondary famine conditions and the other involving biomass that is only subjected to primary feast and famine conditions.

It was clear that the biomass enriched in the SBR with secondary perturbation (SBR-(B1)) exhibited an enhanced capacity for PHA-accumulation compared to the control SBR (SBR-A), as shown in FIG. 9. Whereas the biomass enriched in the control SBR-A reached PAP of 37% g-PHA/g-VSS after 24-29 h, the biomass from SBR-(B1) exhibited PAP of 49-57 g-PHA/g-VSS within the same amount of time.

The maximum (initial) specific rate of PHA production was similar between SBR-A and SBR-(B1) at the same time of operation. However, these rates decreased gradually over SBR operation time from 0.08-0.09 g-PHA/g-X/h before day 10 to 0.03-0.04 g-PHA/g-X/h after day 25. A similar time trend was also observed for the yield of PHA over substrate, decreasing from 0.4 to 0.2 g-PHA/g-Acetate over the course of the SBR operations. These trends in time were likely due to the fact that the SBRs were inoculated, in part, with a biomass that was already well enriched using a more favorable substrate from a wet-oxidation process containing relatively high levels of RBCOD. Thus, developments in the kinetics of accumulation were similar and were understood to be due to the history of biomass and the biomass adaptation to the specific SBR primary perturbation conditions using a municipal wastewater. Notwithstanding that these similar trends of biomass acclimation occurred over time in parallel in SBR-A and SBR-(B1), the biomass harvested from SBR-(B1) still consistently exhibited a much higher PAP after 24 h of accumulation than the biomass harvested from the control SBR-A that did not experience any form of secondary perturbation.

In a separate set of experiments, biomass harvested from SBR-A, SBR-(B1), and (B2) were assessed for PAP in parallel. The biomass samples for these experiments were taken on the same day such that a possible influence in the observed differences between respective biomass PAP performance due to the number of days of enrichment could be controlled for. For these experiments, a slightly different assessment method was employed based on standard additions of substrate from a concentrated solution (100 g-Acetate/L with N&P in a COD:N:P ratio of 100:1:0.05) at the start of the accumulation experiment (1 g-Acetate/L in the accumulation reactor) and after 5 h (0.5 g-Acetate/L), followed by continuous feeding of 200 mL of the substrate solution from 8 to 24 h.

Figure 10:
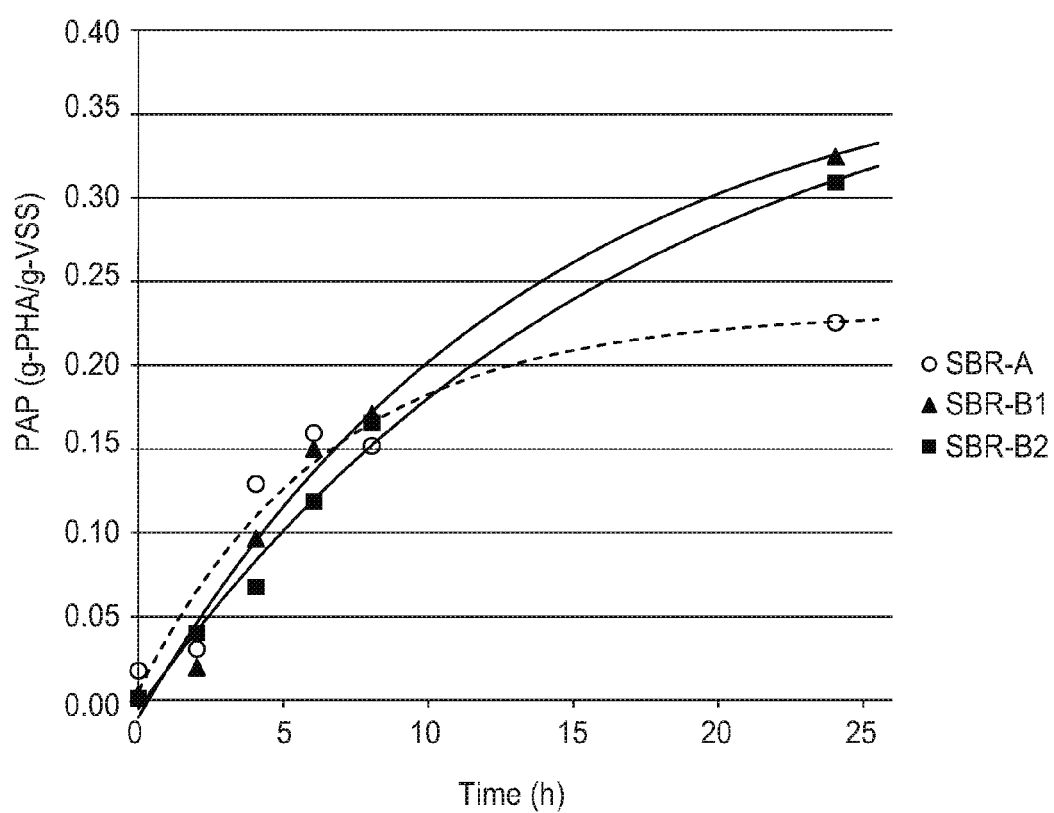
FIG. 10 is another graphical illustration showing PHA accumulation potential for parallel processes.

A positive effect on PAP from the process with secondary perturbation was similarly observed in these accumulation experiments (FIG. 10). The PAP of the biomass from SBR-(B1) and (B2) were 32% and 31% g-PHA/g-VSS, respectively, whereas the biomass from the control SBR expressed a PAP of only 23% g-PHA/g-VSS. The levels of PAP were found to be generally lower in this specific set of experiments and this decrease was considered to be due to the less than optimal conditions and methods employed for PHA accumulation that were applied for this particular assessment. Relatively high background substrate concentrations were observed throughout the accumulation, and particularly during the overnight period, which may be inhibitive to the biomass. Such inhibitory substrate levels were avoided in the assessments where a feed-on-demand strategy of substrate supply was applied. Thus, one may consider that PAP is not only related to the history of the biomass, but it is also sensitive to the methods of accumulation that are applied.

In conclusion, secondary perturbation carried out in a separate sidestream reactor where famine conditions were applied, such that the retention time of secondary famine was longer than the cycle time of primary famine in feast-famine selection and less than the SRT of the biomass, contributed significantly in the observed PHA accumulation potential relative to a process where the same primary (feast and famine) perturbation was applied without any secondary perturbation.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. A method of biologically treating wastewater with biomass and enhancing PHA accumulation potential of the biomass, comprising:

mixing the wastewater with the biomass and biologically treating the wastewater to remove contaminants from the wastewater; and enhancing the PHA accumulation potential of the biomass by:
  i. subjecting the biomass to repeated cycles of a primary feast-famine process wherein:
    a. the biomass is subjected to primary feast conditions;
    b. the biomass is subjected to primary famine conditions; and
    c. the primary feast and primary famine conditions are repeated at least once;
  ii. after subjecting the biomass to repeated cycles of the primary feast-famine process, applying a secondary famine process that comprises subjecting at least a fraction of the biomass to secondary famine conditions for a period of time that is substantially greater than the average time period of the primary famine conditions.

2. The method of claim 1 wherein the biomass is subjected to secondary famine conditions on average for a period of time that is less than 6 days.

3. The method of claim 1 wherein the method is carried out in a sequencing batch reactor (SBR) and includes biologically treating the wastewater in the SBR and subjecting the biomass 25 to the primary feast-famine process in the SBR; and wherein after the biomass has been subjected to primary famine conditions in one cycle of the primary feast-famine process, deviating from the primary feast-famine process and subjecting the biomass in the SBR to the secondary famine conditions.

4. The method of claim 1 carried out in an SBR and a sidestream reactor and including conducting the primary feast-famine process in the SBR and transferring at least a portion of the biomass from the SBR to the sidestream reactor and subjecting the biomass in the sidestream reactor to the secondary famine conditions.

5. The method of claim 4 wherein at least a portion of the biomass is transferred back and forth between the SBR and the sidestream reactor and wherein the primary feast-famine process is carried out in the SBR and the biomass is subjected to the secondary famine conditions in the sidestream reactor.

6. The method of claim 4 wherein the biomass is contained within mixed liquor in the SBR and the method includes subjecting the biomass to repeated feast and famine conditions in the SBR and instigating secondary famine treatment of the biomass while the biomass in the SBR is being subjected to primary famine conditions by transferring at least a portion of the biomass from the SBR to the sidestream reactor and subjecting the biomass in the sidestream reactor to secondary famine conditions.

7. The method of claim 4 wherein each primary feast-famine cycle includes a primary feast period and a primary famine period; and the method includes maintaining the period of time that the biomass is subjected to secondary famine conditions in the sidestream reactor to a time period greater than the average primary famine period but less than 6 days.

8. The method of claim 1 including a continuous flow mainstream process where the primary feast-famine process is carried out in a mainstream; and wherein the secondary famine process is carried out in a sidestream.

9. The method of claim 8 wherein the mainstream includes a primary feast reactor and a primary famine reactor and the method includes subjecting the biomass to primary feast conditions in the primary feast reactor and subjecting the biomass to primary famine conditions in the primary famine reactor; wherein the sidestream includes a secondary famine reactor and the method includes subjecting the biomass to secondary famine conditions in the secondary famine reactor; and the method further includes transferring biomass back and forth between the primary famine reactor and the secondary famine reactor.

10. The method of claim 1 including carrying out the primary feast-famine process in a mainstream; settling at least a portion of the biomass after the biomass has been subjected to at least one primary feast-famine cycle; and transferring at least a portion of the settled biomass to a secondary famine reactor and subjecting biomass in the secondary famine reactor to the secondary famine conditions before returning biomass back to conditions of primary feast-famine conditions.

11. The method of claim 10 wherein the secondary famine reactor is located in a sidestream.

12. The method of claim 10 wherein there is a return biomass line for directing at least a portion of the settled biomass from a solids-liquid separator to the mainstream; and wherein the method includes transferring biomass back and forth between the return biomass line and the secondary famine reactor and subjecting the biomass in the secondary famine reactor to the secondary famine conditions.

13. The method of claim 1 including:
subjecting the biomass to the primary feast-famine process by directing the biomass into and through feast and famine reactors in a mainstream and thereafter settling at least a portion of the biomass and returning the settled biomass to the feast and famine reactors in the mainstream where the biomass is subjected to alternating feast and famine conditions; and
subjecting at least a portion of the returning biomass to the secondary famine conditions after which the biomass is returned to the mainstream and directed into and through the feast and famine reactors therein.

14. The method of claim 13 wherein the secondary famine reactor communicates with a biomass return line that is operatively connected between a solids-liquid separator and the mainstream.

15. The method of claim 1 including:
directing the biomass into a primary feast reactor in a mainstream and subjecting the biomass to primary feast conditions in the primary feast reactor;
after the biomass has been subjected to primary feast conditions, directing the biomass to a downstream primary famine reactor in the mainstream and subjecting the biomass to primary famine conditions in the primary famine reactor;
after the biomass has been subjected to primary famine conditions, directing the biomass to a solids-liquid separator and separating the biomass from treated wastewater;
recycling the separated biomass to the mainstream and repeatedly directing the separated biomass through the primary feast and famine reactors;
continuing to recycle separated biomass to the primary feast and famine reactors for a selected time period;
periodically or continuously directing the at least a portion of the separated biomass to a secondary famine reactor and subjecting the biomass to secondary famine conditions in the secondary famine reactor; and
after the separated biomass has been subjected to secondary famine conditions, directing at least a portion of this biomass back to the mainstream and subjecting the biomass to repeated feast and famine conditions in the mainstream.

16. The method of claim 15 wherein the biomass treated in the secondary famine reactor was treated in the primary feast reactor and then in the primary famine reactor before reaching the secondary famine reactor.

17. The method of claim 1 wherein the primary feast and famine conditions are carried out in primary feast and famine reactors and wherein the secondary famine is carried out in a secondary famine reactor, and wherein the primary feast reactor is disposed in a mainstream and the primary famine reactor is disposed in a first sidestream and the secondary famine reactor is disposed in a second sidestream reactor; and wherein the method includes:
   subjecting the biomass to primary feast conditions in the primary feast reactor;
   after subjecting the biomass to primary feast conditions in the primary feast reactor, directing the biomass to a solids-liquid separator and separating biomass from mixed liquor;
   directing the separated biomass to the primary famine reactor and subjecting the separated biomass to primary famine conditions;
   cycling the biomass through the primary feast reactor, solids-liquor separator and the primary famine reactor and back to the primary feast reactor a selected number of cycles; and
   transferring at least a portion of the biomass from the primary famine reactor to the secondary famine reactor and subjecting this biomass in the secondary famine reactor to secondary famine conditions; and
   returning at least of portion of the biomass in the secondary famine reactor back to the rest of the biomass that is cycling through primary feast and famine reactor.

18. The method of claim 17 wherein the solids-liquid separator is operatively interconnected between the primary feast reactor and the primary famine reactor and wherein the biomass is subjected to primary famine conditions after the biomass has been subjected to primary feast conditions in the main stream and after the biomass has been separated from mixed liquor by the solids-liquid separator.

19. The method of claim 1 wherein the biomass is subjected to secondary famine conditions for a period of time that is greater than or equal to the average primary feast-famine retention time or cycle time.

20. The method of claim 1 including carrying out the primary feast process in a mainstream; settling at least a portion of the biomass after the biomass has been subjected to primary feast conditions and subjecting the biomass to primary famine conditions in a sidestream reactor; wherein at least a portion of the biomass is exchanged back and forth between the sidestream reactor and a secondary sidestream famine reactor so as to expose biomass to conditions of secondary famine also in a sidestream.

21. The method of claim 1 including:
   carrying out a portion of the primary famine process in a mainstream;
   settling at least a portion of the biomass after the biomass has been subjected to primary feast conditions and primary famine conditions in the mainstream;
   carrying out another part of the primary famine process in a sidestream where the biomass is subjected to primary famine conditions in the sidestream;
   subjecting the biomass to the secondary famine process in a secondary sidestream reactor; and
   transferring the biomass back and forth between the secondary famine sidestream and the primary famine sidestream reactors.

22. The method of claim 18, wherein primary famine is achieved in part before the solids-liquid separator.

23. The method of claim 1 wherein substantially all of the biomass is subjected to secondary famine conditions at one time.

24. The method of claim 1 where in only portions of the total process biomass are repeatedly subjected to secondary famine conditions at any given time.

25. The method of claim 24 including repeatedly subjecting portions of the biomass to secondary famine conditions such that statistically all of the biomass is on average conditioned by the effect of extended famine conditions imparted by the secondary famine process.

26. The method of claim 1 wherein the biomass in the process is subjected to secondary famine conditions on average at least once every four solids retention times (SRTs) for the biomass in the process.

27. A method of biologically treating wastewater with biomass and enhancing PHA accumulation potential of the biomass comprising:
   directing a wastewater stream containing readily biodegradable chemical oxygen demand (RBCOD) and nitrogen into a primary feast reactor;
   maintaining anoxic conditions in the primary feast reactor and subjecting the biomass to primary feast conditions while denitrifying the wastewater;
   directing the wastewater and biomass from the primary feast reactor to a downstream primary famine reactor;
   maintaining aerobic conditions in the primary famine reactor and subjecting the biomass to primary famine conditions while nitrifying the wastewater;
   recirculating the wastewater and biomass from the primary famine reactor to the primary feast reactor to give rise to a primary feast-famine process where the biomass is subjected to repeated cycles of primary feast and famine conditions;
   after at least a portion of the biomass has been subjected to repeated cycles of primary feast and famine conditions in the primary feast reactor and the primary famine reactor, directing the wastewater and biomass from the primary famine reactor to a secondary famine reactor; and
   subjecting the biomass in the secondary famine reactor to a secondary famine process where the biomass is subjected to secondary famine conditions for a period of time substantially greater than the average time period that the biomass was exposed to primary famine conditions in the primary famine reactor.

28. The method of claim 27 including operating the secondary famine reactor under anoxic conditions and denitrifying wastewater in the secondary famine reactor.

29. The method of claim 27 wherein the method includes a solids retention time (SRT) for the suspended biomass in the process, and the method includes retaining the biomass in the secondary famine reactor for a period of time less than the SRT.

30. The method of claim 27 including directing the wastewater and biomass from the secondary famine reactor to a solids-liquid separator and separating the biomass from the wastewater; and recycling the separated biomass to the primary feast reactor and/or primary famine reactor.

31. The method of claim 27 wherein the average flow rate of the separated biomass recycled to the primary feast reactor and/or primary famine reactor is between 0.2 and 2.0 times the average flow rate of the wastewater stream directed to the primary feast reactor.

32. The method of claim 27 wherein the wastewater and biomass form a part of mixed liquor and wherein the flow rate of mixed liquor recycled from the primary famine reactor to the primary feast reactor is between one and five times the average flow rate of the wastewater directed into the primary feast reactor.

* * * * *